United States Patent [19]

O'Keefe

[11] Patent Number: 5,322,795
[45] Date of Patent: Jun. 21, 1994

[54] HPLC ASSAY FOR THE SELECTIVE RESOLUTION OF RECOMBINANT PROTEINS

[75] Inventor: Donald O'Keefe, Bedminster, N.J.
[73] Assignee: Merck & Co., Inc., Rahway, N.J.
[21] Appl. No.: 902,618
[22] Filed: Jun. 23, 1992
[51] Int. Cl.[5] .................. G01N 21/64; G01N 33/533; G01N 33/68
[52] U.S. Cl. ..................................... 436/86; 436/161; 436/172
[58] Field of Search ................... 436/86–90, 436/161, 172, 175, 178; 530/344, 412–417

[56] References Cited

PUBLICATIONS

Pande, C. et al. "Characterization of the fluorescent bimane derivative of *E. coli* initiator transfer RNA". Biochem. Biophys. Res. Commun.; 127(1), pp. 49–55, 1985.
Cotgreave et al. "Methodologies for the application of monobromobimane to the simultaneous analysis of soluble and protein thiol components of biological systems". J. Biochem. Biophys. Methods, 13(4–5), 231–49, 1986.
Svardal et al. "Determination of reduced, oxidized, and protein-bound glutathione in' human plasma with precolumn derivatization with monobromobimane and liquid chromatography". Anal. Biochem., 184(2), pp. 338–346, 1990.
P. C. Chinn, et al; *Determination of Thiol Proteins Using Monobromobimane Labeling and High-Performance Liquid Chromatographic Analysis: Application to Escherichia coli and Thioredoxin;* Analytical Biochemistry 159, pp. 143–149 (1986).

Primary Examiner—James C. Housel
Assistant Examiner—David Redding
Attorney, Agent, or Firm—Joseph F. DiPrima; Mark R. Daniel; David A. Muthard

[57] ABSTRACT

Proteins that cannot be resolved by conventional HPLC techniques, including reversed-phase HPLC, can be distinguished, and the quantity of a protein of interest monitored in numerous types of in-process samples, including fermentation and down-stream processing samples, by covalently binding monobromobimane to a protein of interest bearing sulfhydryl groups and chromatographing these in-process samples using reversed-phase HPLC, fluorescence detection and UV absorbance detection.

1 Claim, 6 Drawing Sheets

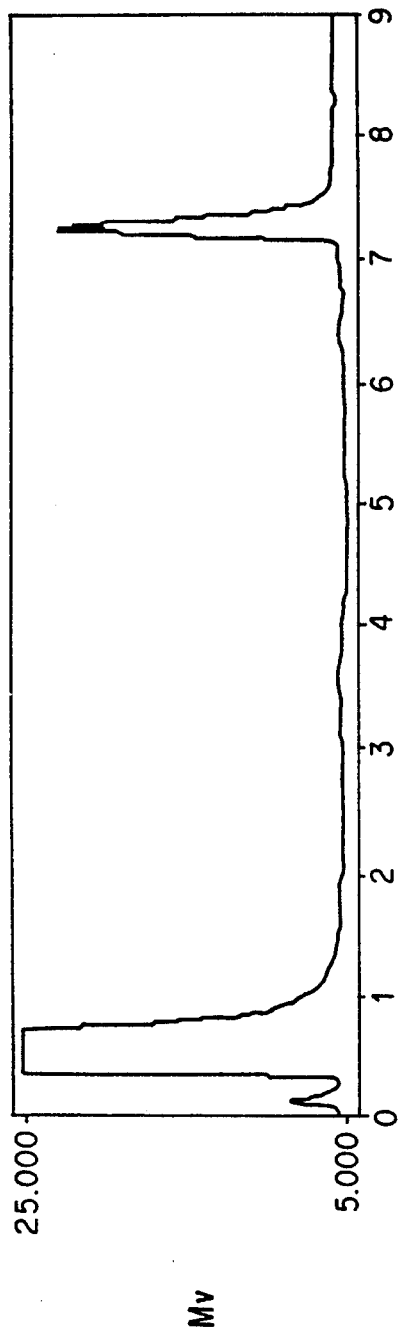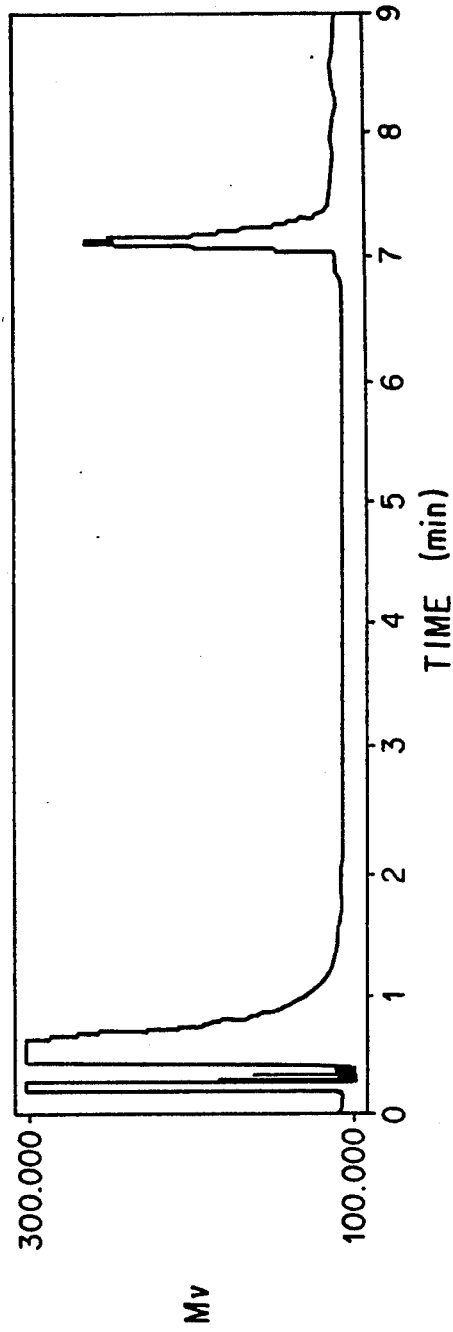

HPLC ASSAY FOR THE SELECTIVE RESOLUTION OF RECOMBINANT PROTEINS

BACKGROUND OF THE INVENTION

Reversed-phase high performance liquid chromatography (HPLC) is generally a highly useful technique for resolution of different proteins. A problem, however, exists in the chromatography art in that on occasion, HPLC cannot resolve proteins that one would ordinarily expect to resolve on the basis of different physicochemical properties. For example, TGFαPE$_{40}$ab and PE$_{40}$ab, which differ in length by approximately 50 amino acid residues, were unexpectedly found to resist resolution by reversed-phase HPLC. Numerous attempts were made using a number of different columns under a variety of mobile phase conditions. The types of columns tried included different silica-based columns with varying length hydrocarbonaceous ligates as well as wide-pore polystyrene divinylbenzene polymeric resins. Various mobile phases at pH 2, 4.5, 7, 8.5, and 10 were evaluated, as were a number of organic modifiers. In all cases, TGFαPE$_{40}$ab could not be resolved satisfactorily from PE$_{40}$ab.

Pseudomonas aeruginosa produces the exotoxin Pseudomonas exotoxin A. The exotoxin consists of four structural domains, namely Ia, II, Ib and III. When domain Ia is cleaved off the exotoxin, the resulting protein is known as PE$_{40}$. Transforming growth factor alpha (TGFα) can be genetically fused to the amino terminus of PE$_{40}$ to produce the chimeric protein TGFαPE$_{40}$. When cysteine residues in domain II of PE$_{40}$ are deleted or substituted by non-cysteinyl amino acids, the resulting protein is PE$_{40}$ab, which when genetically fused to TGFα produces TGFαPE$_{40}$ab. The TGFα portion of the hybrid will still contain cysteine residues. Thus, PE$_{40}$ab and TGFαPE$_{40}$ab can be differentiated on the basis of presence or absence of cysteine residues.

TGFαPE$_{40}$ab is useful in treatment of certain tumor cells. Its manufacture involves a fermentation process that requires a rapid assay that can monitor the product at each step of manufacturing from fermentation to the final product. TGFαPE$_{40}$ab is an intracellular product which, in the early stages of growth, represents only a small percentage of the total amount of cellular protein. Reversed-phase HPLC was able to resolve TGFαPE$_{40}$ab from the host cell proteins, but was not able to resolve it from PE$_{40}$ab. This caused inaccurate quantitation of expression levels of TGFαPE$_{40}$ab. This additionally caused the problem of being unable to estimate recovery and yield of each step in the purification process. Although, PE$_{40}$ab and TGFαPE$_{40}$ab can be resolved by western blot analysis, this technique is impractical for monitoring commercial scale batches. Therefore, a need exists in the art for a method of assaying proteins that differ in physicochemical properties, such as size, but are not resolved by reversed-phase HPLC. The present invention meets that need by exploiting the presence or absence of cysteinyl amino acid residues between two or more proteins.

BRIEF DESCRIPTION OF THE DRAWINGS

FIG. 3 shows two chromatograms of mBBr-labeled TGFαPE$_{40}$ab. The top chromatogram shows ultraviolet detection at 280 nm. The bottom chromatogram shows fluorescence.

SUMMARY OF THE INVENTION

The invention is an assay for quantifying relative amounts of a protein of interest in numerous types of in-process samples, including both fermentation and down-stream processing samples, and that can be used when the protein of interest contains one or more amino acid residues not found in the other proteins, or when the protein of interest lacks one or more such amino acid residues found in the other proteins. The assay comprises the steps of fluorescently labeling the amino acid(s), or their derivatives, that are not common to both the protein of interest and the other protein(s), chromatographing an aliquot from the labeled in-process sample in a reversed-phase HPLC apparatus and detecting for fluorescence. Preferably, such amino acids will be sulfhydryl-containing residues. An additional embodiment of the invention is that sulfhydryl groups can be chemically bonded to amino acid residues on which sulfhydryls are not naturally found, in order to create a class of proteins bearing sulfhydryl residues that can be differentiated from other proteins by the assay of the invention.

DETAILED DESCRIPTION OF THE INVENTION

Cysteine residues located exclusively in the protein of interest are exploited by labeling them with the sulfhydryl-specific reagent monobromo-bimane (mBBr). Cysteine, containing a thiol group, is the most reactive amino acid in proteins. At alkaline pH the thiol group ionizes, forming a thiolate anion, which is generally the reactive species.

mBBr is a member of a class of heterocyclic compounds called bimanes that specifically react with thiols, forming a fluorescent product. Once formed, the fluorescently labeled product is stable to air, many chemical and biochemical reactions, and resists fading during exposure to irradiation. These properties make mBBr well suited to sulfhydryl analysis. The mBBr reaction is complete in less than one minute and for TGFαPE40ab can detect as low as 17.7 pmoles of sulfhydryls. It will be readily appreciated by those of ordinary skill in this art that not all sulfur-containing residues in a given protein will be sulfhydryls that render themselves accessible to covalent bonding to a fluorescent labeling agent such as mBBr. Therefore, it is an additional aspect of the present invention that relative quantitation of proteins may take place where both the protein of interest and the unwanted proteins have sulfur-containing residues present, but only one of these has sulfhydryls that render such sulfhydryls accessible to a fluorescent labeling agent such as mBBr.

Figure 6:
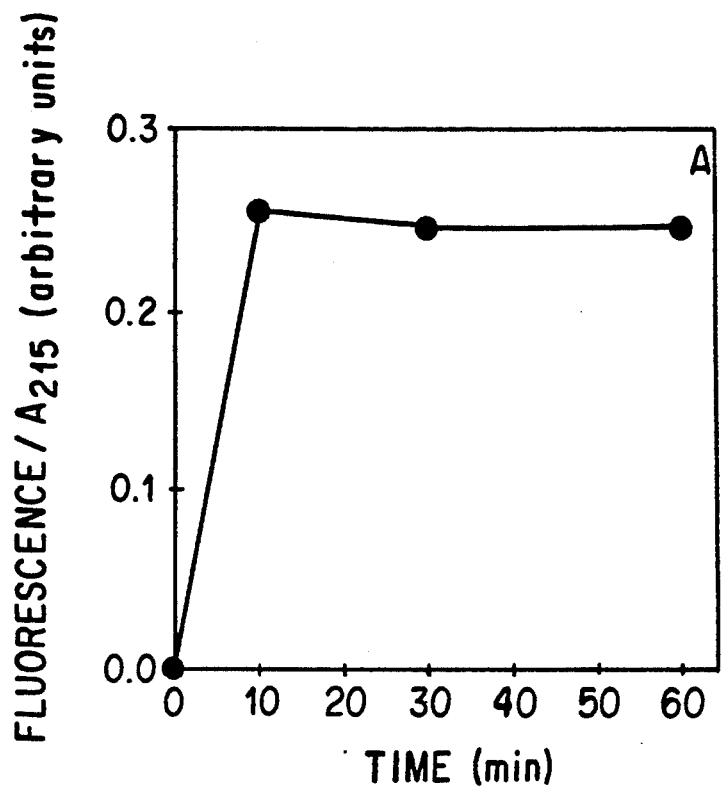
FIG. 6 is a graph showing the time course of mBBr incorporation into the protein thiols of aFGF.
Figure 7:
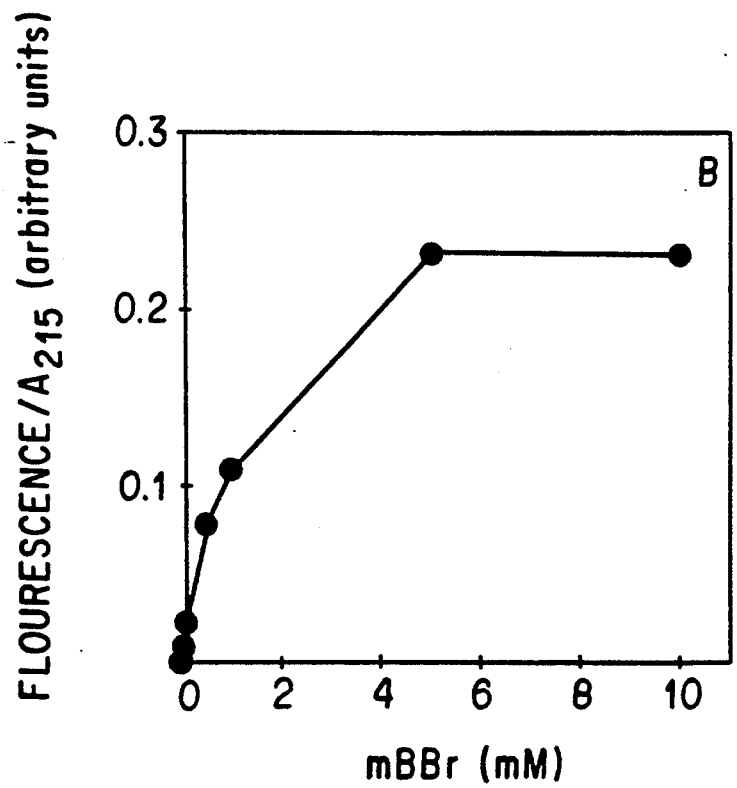
FIG. 7 is a graph showing the concentration-dependent incorporation of mBBr labels into aFGF thiols.

A procedure for labeling protein thiols with mBBr was developed with recombinant aFGF as a model protein. The time course of mBBR incorporation into protein thiols is shown in FIG. 6. The results demonstrate that the reaction is rapid and reaches completion in less than ten minutes. FIG. 7 shows the concentration-dependent incorporation of mBBr labels into aFGF thiols, demonstrating that sulfhydryl labeling was maximal at about 5 mM.

Figure 8:
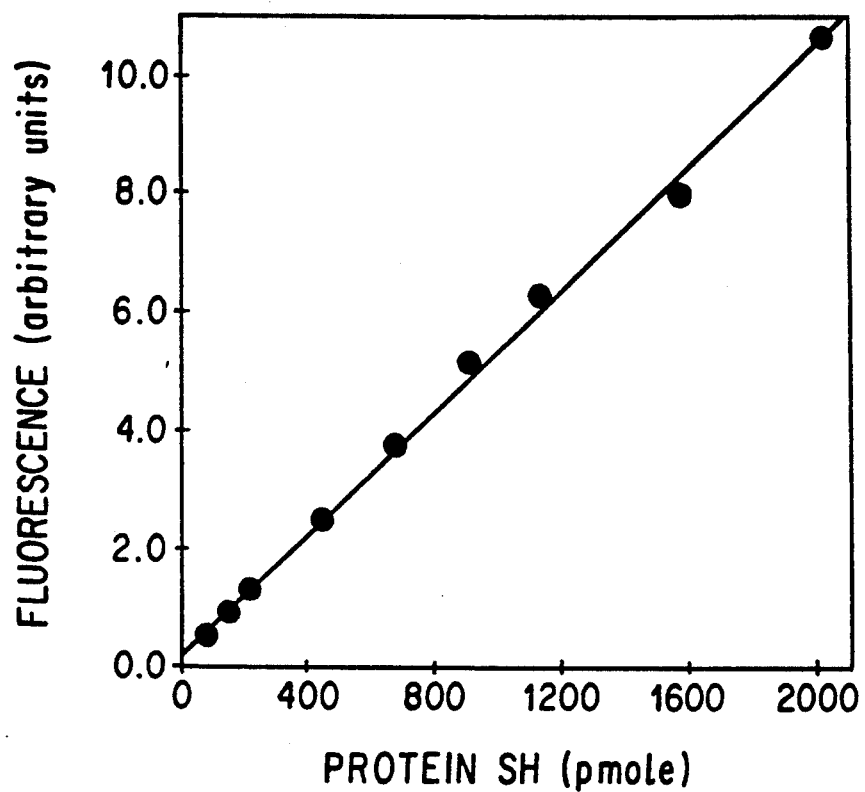
FIG. 8 is a graph showing the linear range of fluorescent sulfhydryl detection for aFGF.

Protein thiol labeling with mBBr was found to be both sensitive and quantitative. After labeling aFGF with mBBr, different amounts of protein were chromatographed and the results plotted versus the number of protein sulfhydryls. The results, shown in FIG. 8, demonstrate that the assay was linear from 90 to 2025 pmoles of aFGF sulfhydryls (0.48–10.8 μg of aFGF).

Prior to mBBr labeling, the protein(s) are denatured and reduced. A preferred reducing agent is dithiothreitol (DTT). A preferred denaturing agent is sodium dodecyl sulfate (SDS).

The approach for fluorescently labeling a protein bearing cysteines with mBBr for in-process monitoring and quantitation may be extended to other difficult-to-resolve proteins. There are a variety of other fluorescent compounds that are reactive with amine and carboxylic acid side chains in proteins, well known to those of skill in the art. Additionally, fluorescent reagents are known that react with carbohydrates. Thus, the invention can be used where such amino acids exist compared to an impurity lacking such amino acids, or in the case of recombinant proteins derived from mammalian cells, where glycosylation exists that is lacking in an impurity. Those of ordinary skill in the art will readily appreciate that such amino acids can be readily engineered into proteins to provide the necessary site for fluorescent labeling to facilitate in-process monitoring and quantitation.

The following non-limiting examples further illustrate details for the practice of the present invention. Those skilled in the art will readily understand that known variations of the conditions and processes of the following preparative procedures can be used. The entire disclosure of the references cited below is incorporated herein by reference.

EXAMPLE 1

Materials

TFA and DTT were obtained from Pierce (Rockford, Ill.). Tris base was purchased from Boehringer Mannheim (Indianapolis, Ind.). Acrylamide was acquired from National Diagnostics (Manville, N.J.). Other electrophoresis reagents and rabbit anti-goat antibody conjugated to alkaline phosphatase were purchased from Bio-Rad (Richmond, Calif.). HPLC-grade acetonitrile was acquired from Fisher. Other reagents were obtained from either Fisher or Sigma. TGFαPE40ab containing impurities of PE40ab was obtained from Merck Research Laboratories (West Point, Pa.).

Western Blots

Protein samples were electrophoresed through 12% polyacrylamide SDS gels according to the method of Laemmli. Nature, 227 (1970) 680. The samples did not contain reducing agent and were not heated prior to electrophoresis. After electrophoresis, proteins were transferred to nitrocellulose paper (Schleicher & Schuell, Keene, N. H.) in a Genie electroblotter (Idea Scientific, Minneapolis, Minn.) as described by Towbin et al, Proc. Natl. Acad. Sci. USA, 76 (1979) 4350, except the transfer buffer was made 0.1% SDS. Proteins bound to the nitrocellulose paper were then probed with either goat anti-TGFα antisera (Biotope, Redmond, Wash.) or goat anti-PE antisera (List Biologicals, Campbell, Calif.) as described by Tweten et al J. Bacteriol., 156 (1983) 680. Immunoreactive proteins were then detected using rabbit anti-goat antibody conjugated to alkaline phosphatase according to the methods of Blake, et al Anal. Biochem., 136 (1984) 175 and Pluzek et al CRC Handbook of Immunoblotting of Proteins, CRC Press, Inc., 1988, Vol. 1, p. 177. Control experiments demonstrated that these antisera did not cross react with E. coli proteins.

EXAMPLE 2 mBBR was obtained from Molecular Probes (Eugene, Oreg.). The product is nonfluorescent and stable when stored in the dark. mBBr was prepared as a 100 mM solution in acetonitrile. the solution was stable and protected from photolysis when stored at 4° C. in a wrapped brown bottle according to the method of Kosower et.al., Methods Enzymol. Vol. 143, p. 76–84 (1987). Stock solutions of 30 mM EDTA and 10% SDS were stored at room temperature. Solutions of 30 mM dithiothreitol (DTT) and 40 mM cysteine were made fresh.

Proteins were labeled with mBBr following 30 min incubation in 200 mM Tris-HCl, pH 8.0/3 mM EDTA/3 mM DTT/1% SDS at room temperature. Afterwards, mBBr was added to 5 mM (in subdued light) and the reaction proceeded for 10 min in the dark. The reaction was stopped by a 10-fold dilution into 4 mM cysteine.

The labeled proteins were analyzed by reversed-phase high performance liquid chromatography. The components of the HPLC system were as follows:
1) Spectro Vision FD-200 fluorescence detector with a 382 nm excitation wavelength and a 470 nm emission wavelength. The high voltage of the detector was generally set at 900.
2) Spectroflow 757 variable wavelength absorbance detector.
3) Waters Model 680 Automated Gradient Controller.
4) Waters Model 712 WISP autosampler.
5) Waters Model 510 HPLC pump.
6) Waters Model M-6000A HPLC pump.

Chromatography Procedures aFGF:
  Column: VYDAC C4 (0.46 cm×15 cm, 5 μ particle size, 300 Å pore size)
  Solvent A: 0.1% TFA in water Solvent B: 0.1% TFA in acetonitrile
Flow rate: 2.0 ml/min
Gradient (linear): 75%–40% solvent A in 20 min
TGFαPE$_{40}$ab:
Column: VYDAC C$_4$ (0.46 cm×15 cm, 5 μ particle size, 300 Å pore size)
Solvent A: 0.1% TFA in 20% acetonitrile
Solvent B: 0.1% TFA in 80% acetonitrile
Flow rate: 1.0 ml/min
Gradient (linear): 80%–20% solvent A in 40 min

EXAMPLE 3

To expose cysteine sulfhydryls, purified protein and in-process samples of TGFαPE$_{40}$ab were denatured and reduced in 200 mM Tris-HCl, pH 8.0, 1% SDS, 3 mM EDTA, 3 mM DTT for 20 min at room temperature. mBBr (Molecular Probes, Euguene, Oreg.) was added to a final concentration of 15 mM from a 100 mM stock solution in acetonitrile. The reaction proceeded for 2 min at room temperature in subdued light before it was terminated by a 10-fold dilution into 4 mM cysteine. Cysteine and DTT stock solutions were made fresh.

Chromatography

Proteins were chromatographed on a HY-TACH non-porous C$_{18}$ column (30 mm×4.6 mm) from Glycotech, Inc. with a linear gradient of 34% to 64% acetonitrile in 0.1% TFA over 6 min at 1.0 ml/min. The column was equipped with a water jacket equilibrated at 80° C. by a Lauda RM6 circulating water bath. Control experiments demonstrated that TGFα-PE$_{40}$ab remained intact during the short time it was exposed to elevated temperature. UV absorbance was at 280 nm and fluorescence detection was at 470 nm after excitation at 382 nm. The chromatography system consisted of a Waters Model 712 WISP autosampler and a Waters Model 680 automated gradient controller controlling Waters Model 510 and Model M-6000 pumps. A Spectroflow 757 variable wavelength absorbance detector from Applied Biosystems and a Spectro Vision FD-200 fluorescence detector were in-line to monitor column effluent.

Figure 1:
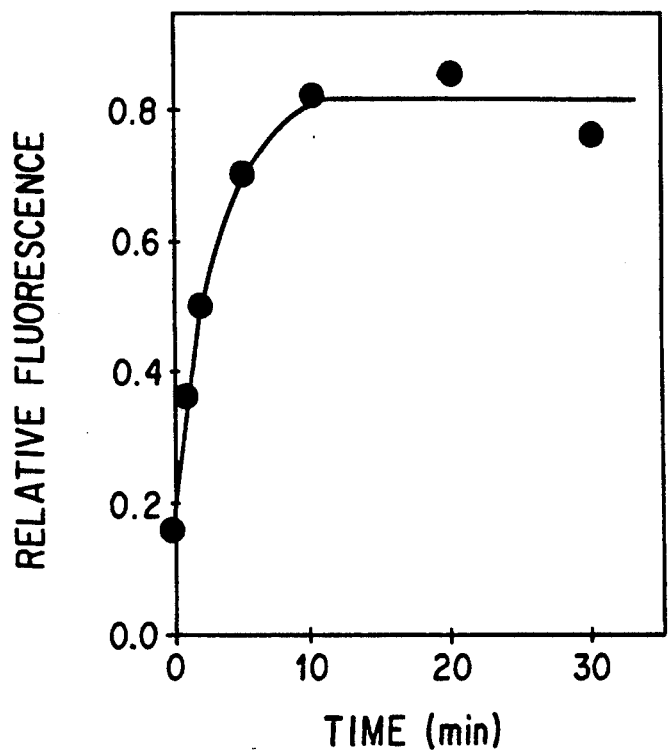
FIG. 1 is a graph showing the kinetics of disulfide reduction in TGFαPE$_{40}$ab.
Figure 2:
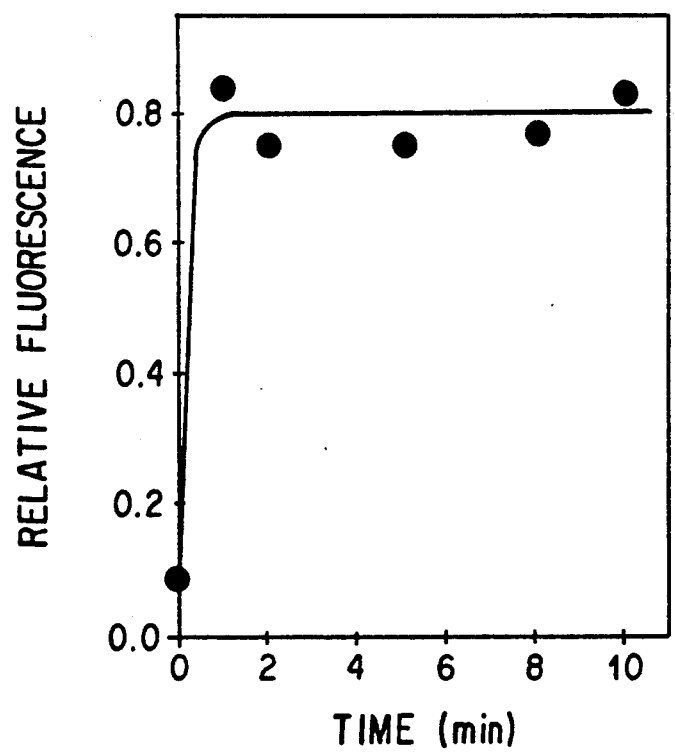
FIG. 2 is a graph showing the kinetics of mBBr labeling in TGFαPE$_{40}$ab.
Figure 4:
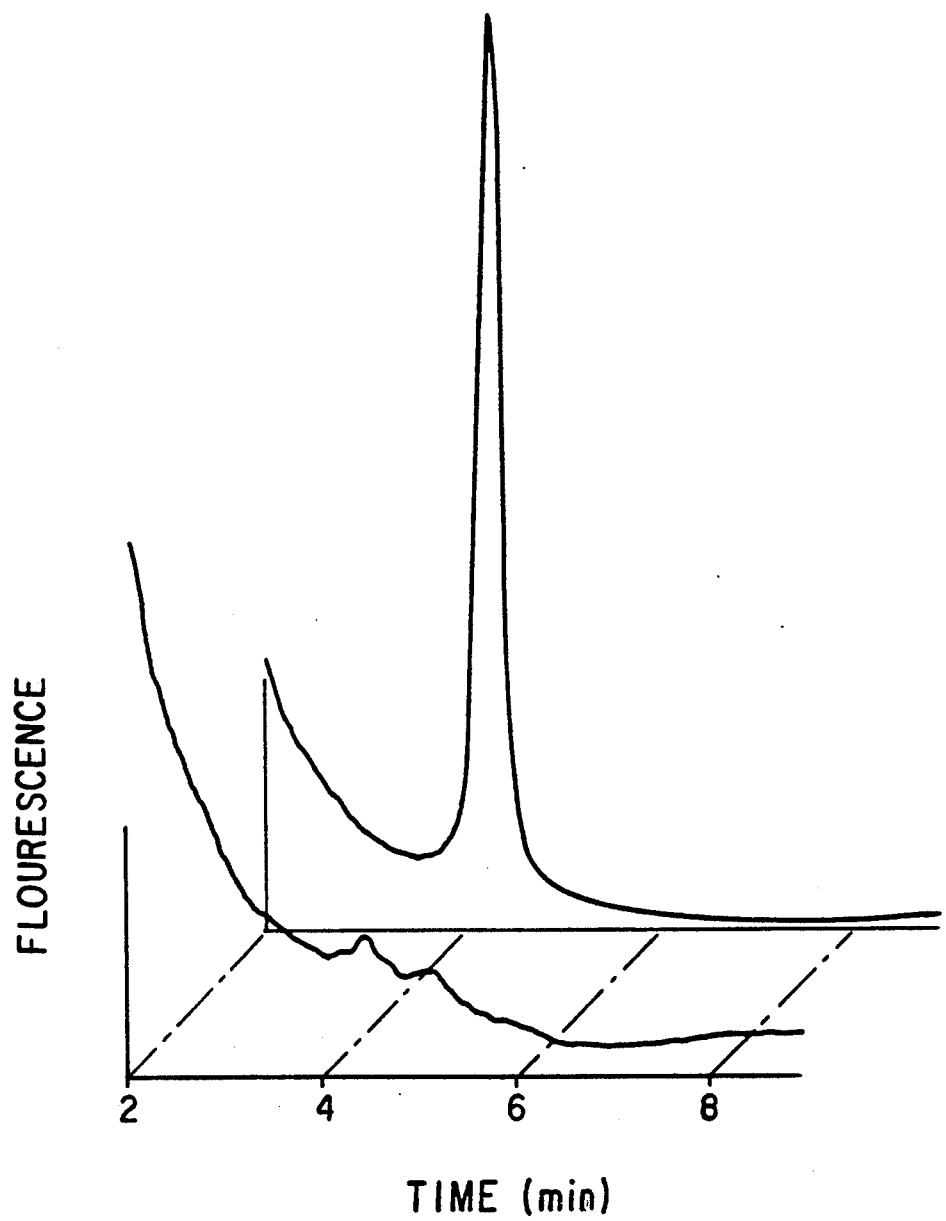
FIG. 4 shows reversed-phase chromatograms of equivalent amounts of TGFαPE$_{40}$ab and PE$_{40}$ab labeled with mBBr. The top chromatogram represents TGFαPE$_{40}$ab and the bottom chromatogram represents PE$_{40}$ab.
Figure 5:
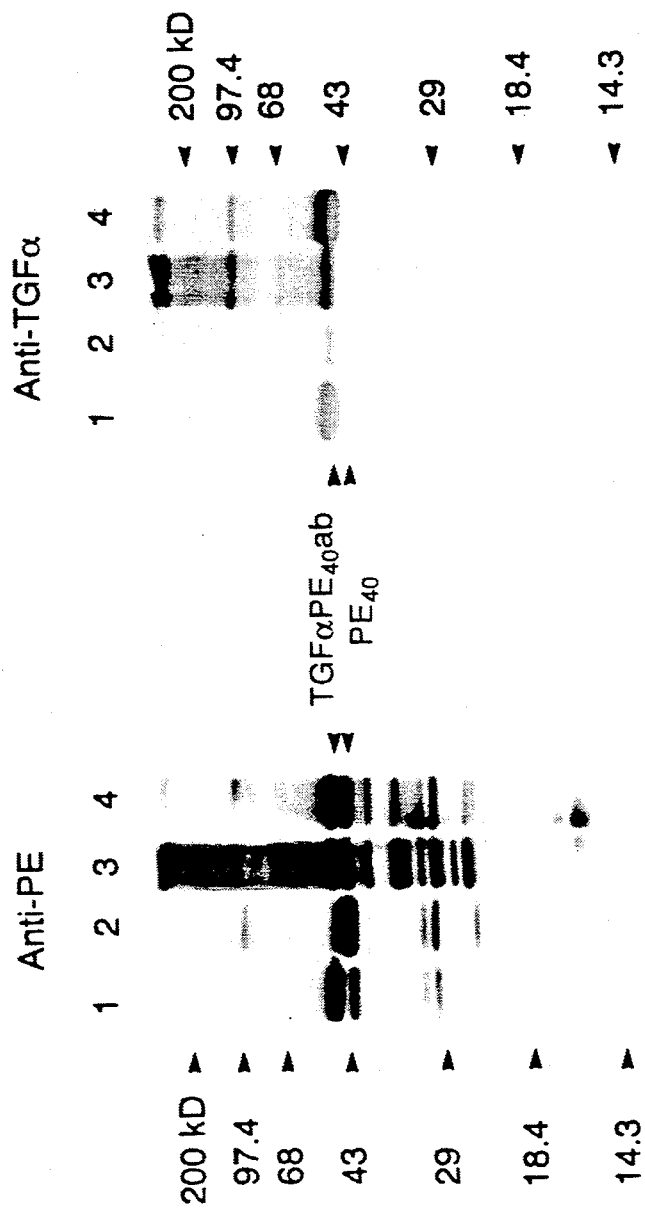
FIG. 5 is a western blot analysis of TGFαPE$_{40}$ab. Proteins transferred to nitrocellulose paper were probed with either anti-exotoxin A (commercially available from List Biologicals, CA) or anti-TGFα antisera. The lanes for each blot correspond to: 1) a TGFα-PE$_{40}$ab enriched sample; 2) a PE$_{40}$ab enriched sample; 3) a cell lysate from Escherichia coli that produced TGFα-PE$_{40}$ab; and 4) a partially purified TGFαPE$_{40}$ab sample. Lanes 1, 3 and 4 within each blot contained the same amount of TGFαPE$_{40}$ab while lane 2 contained an equivalent amount of PE$_{40}$ab. The migration of molecular weight markers (in kilodaltons) are indicated for each blot.

When samples that were highly enriched with TGFαPE$_{40}$ab or with PE$_{40ab}$ were labeled with mBBr and then chromatographed by reversed-phase HPLC, mBBr-labeled TGFαPE$_{40}$ was detected by fluorescence whereas PE$_{40}$ab was not, as shown in FIG. 4. The small peak seen in the mBBr-treated PE$_{40}$ab chromatogram at 4.43 min indicates that approximately 1% TGFαPE$_{40}$ab was in the sample, which corresponds to the anti-TGFα western blot analysis of that sample in FIG. 5, in lane 2 thereof.

While the invention has been described and illustrated in reference to certain preferred embodiments thereof, those skilled in the art will appreciate that various changes, modifications or substitutions can be made therein without departing from the spirit and scope of the invention. It is intended, therefore, that the invention be limited only by the scope of the claims which follow and that such claims be interpreted as broadly as is reasonable.

What is claimed is:

1. An assay for the relative quantitation of TGFα-PE$_{40}$ab protein in an in-process sample which comprises one or more other proteins including PE$_{40}$ab protein, comprising the steps of:
   a) denaturing and reducing the proteins in the sample to expose cysteine residues found in the TGFα-PE$_{40}$ab protein but not in the other proteins;
   b) addition of monobrombimane to fluorescently label said cysteine residues of said TGFαPE$_{40}$ab protein;
   c) chromatographically separating the labelled TGFαPE$_{40}$ab protein from said other proteins;
   d) measuring fluorescence of the labelled TGFαPE$_{40}$ab protein and determining the relative level thereof in said sample.

* * * * *